(12) United States Patent
Kratz et al.

(10) Patent No.: US 9,801,949 B2
(45) Date of Patent: Oct. 31, 2017

(54) COMBINATIONS OF ALBUMIN-BASED DRUG DELIVERY SYSTEMS

(71) Applicant: KTB TUMOR FORSCHUNGSGESELLSCHAFT MBH, Freiburg im Breisgau (DE)

(72) Inventors: Felix Kratz, Ehrenkirchen (DE); Andre Warnecke, Freiburg (DE)

(73) Assignee: KTB TUMOR FORSCHUNGSGESELLSCHAFT MBH (DE)

( * ) Notice: Subject to any disclaimer, the term of this patent is extended or adjusted under 35 U.S.C. 154(b) by 0 days.

(21) Appl. No.: 14/380,190

(22) PCT Filed: Feb. 21, 2013

(86) PCT No.: PCT/EP2013/000513
§ 371 (c)(1),
(2) Date: Aug. 21, 2014

(87) PCT Pub. No.: WO2013/124068
PCT Pub. Date: Aug. 29, 2013

(65) Prior Publication Data
US 2015/0023912 A1   Jan. 22, 2015

(30) Foreign Application Priority Data
Feb. 21, 2012 (EP) .................................... 12001136

(51) Int. Cl.
*A61K 38/07* (2006.01)
*A61K 47/48* (2006.01)
*A61K 31/519* (2006.01)
*A61K 31/704* (2006.01)

(52) U.S. Cl.
CPC ...... *A61K 47/48284* (2013.01); *A61K 31/519* (2013.01); *A61K 31/704* (2013.01); *A61K 38/07* (2013.01)

(58) Field of Classification Search
None
See application file for complete search history.

(56) References Cited

U.S. PATENT DOCUMENTS
2004/0063635 A1   4/2004 Yu

FOREIGN PATENT DOCUMENTS

| DE | WO 2011131314 A1 * | 10/2011 | ........... A61K 31/704 |
|----|---|---|---|
| EP | 1419788 | 5/2004 | |
| EP | 2301531 | 7/2011 | |

OTHER PUBLICATIONS

Xu et al.,"Targeted Albumin-Based Nanoparticles for Delivery of Amphipathic Drugs", Bioconjugate Chemistry, 2011, pp. 870-878.*
Elsadek et al., "Optimization of an Albumin-Binding Prodrug of Doxorubicin That Is Cleaved by Protease-Specific Antigen", ACS Medicinal Chemistry Letters, 2010, pp. 234-238.*
International Search Report and the Written Opinion of the International Searching Authority, PCT/EP2013/000513, KTB Tumorforschungsgesellschaft MBH, dated Jun. 27, 2013.
Desai, N. et al., Antitumor activity, and antiangiogenic activity of nanoparticle albumin-bound nab-rapamycin in combination with nab-paclitaxel, Abstract #3125, Cancer Research, Jan. 15, 2009, vol. 69, Issue 2, Supplement 1.
Fowler, J. Charlotte et al., Dual-isotope lymphoscintigraphy using albumin nanocolloid differentially labeled with 111In and 99mTc, Acta Oncologica, 2007; vol. 46; pp. 105-110.
Kratz, Felix, DOXO-EMCH (INNO-206): the first albumin-binding prodrug of doxorubicin to enter clinical trials, Opin. Expert Investig. Drugs, 2007, 16(6), pp. 855-866.
Warnecke, Andre et al., Synthesis, Cleavage Profile, and Antitumor Efficacy of an Albumin-Binding Prodrug of Methotrexate that is Cleaved by Plasmin and Cathepsin B, Arch. Pham., Chem. Life Sci. 2007, 340, pp. 389-395.
Elsadek, Bakheet et al., Development of a novel prodrug of paclitaxel that is cleaved by prostate-specific antigen: An in vitro and in vivo evaluation study, European Journal of Cancer 46 (2010), pp. 3434-3444.
Elsadek, Bakheet et al., Impact of albumin on drug delivery—New applications on the horizon, Journal of Controlled Release 157 pp. 4-28.
Schmid, Bjorn, et al.; Albumin-Binding Prodrugs of Camptothecin and Doxorubicin with an Ala-Leu-Ala-Leu-Linker That Are Cleaved by Cathepsin B: Synthesis and Antitumor Efficacy; Bioconjugate Chemical; Mar. 23, 2007; pp. 702-716; vol. 18; American Chemical Society.
Chung, Da-Eun, et al.; Development of a novel albumin-binding prodrug that is cleaved by urokinase-type-plasminogen activator (uPA); Bioorganic & Medicinal Chemistry Letters; Jul. 27, 2006; pp. 5157-5163; vol. 16; Elsevier Ltd.
Extended European Search Report for European Patent Application No. 12001136.6, dated Jul. 11, 2012.
European Office Action for European Patent Application No. 12001136.6, dated Dec. 18, 2015.

* cited by examiner

*Primary Examiner* — Lianko Garyu
(74) *Attorney, Agent, or Firm* — McDonald Hopkins LLC

(57) ABSTRACT

The present invention relates to a composition comprising at least two different albumin-based drug delivery systems, as well as to a pharmaceutical composition comprising said composition.

3 Claims, 3 Drawing Sheets

DOXO-EMCH

AW054

EMC-D-Ala-Phe-Lys-Lys(γ-MTX)-OH (EMC = 6-maleimidocaproic acid)

COMBINATIONS OF ALBUMIN-BASED DRUG DELIVERY SYSTEMS

Figure 1A:
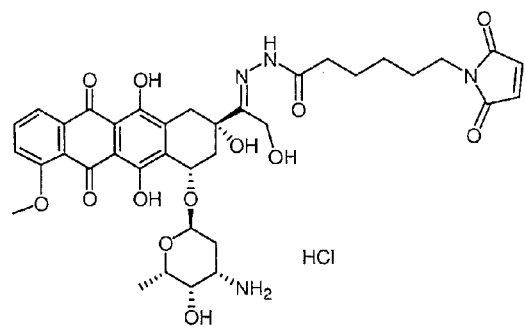

This application is a 35 U.S.C. 371 national stage filing and claims priority to PCT Application No. PCT/EP2013/000513, entitled "Combinations of Albumin-Based Drug Delivery Systems," filed Feb. 21, 2013, which claims the benefit of European Patent Application No. 12001136.6 entitled "Combinations of Albumin-Based Drug Delivery Systems," filed on Feb. 21, 2012, both of which are incorporated by reference herein in their entirety.

The present invention relates to a composition comprising at least two different albumin-based drug delivery systems, as well as to a pharmaceutical composition comprising said composition.

Most of the drugs used at present are compounds having low molecular weights and exhibit, when systemically administered to a patient, a high plasma clearance or total body clearance. Furthermore, said low-molecular weight compounds show a high tendency to penetrate body tissues by diffusion, resulting in a uniform biodistribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytotoxic agents, immunosuppressive agents or virostatic agents.

Several strategies have been pursued for improving the selectivity of low-molecular weight drugs and thus to increase the concentration of the active agent in the desired tissue, while the concentration of the same is decreased in healthy tissues in order to reduce side-effects.

Carriers, such as for example albumin, or its drug conjugates exhibit a markedly long half-life in the systemic circulation of up to 19 days. Because of an elevated permeability of vessel walls of for example malignant, infected or inflamed tissue for macromolecules, the carrier, such as for example serum albumin, accumulates in the target tissue. Accordingly, such albumin-based drug delivery systems represent a promising approach to a more specific and tolerable treatment of such target tissues.

In this context, prodrugs have specifically been presented which bind in situ to e.g. human serum albumin and show improved properties in contrast to the drug alone. In addition, antibodies, peptides or synthetic polymers have been investigated as drug carriers for the development of prodrugs.

However, although such prodrugs have been shown to allow a more specific delivery of the active agent to the target tissue, in most cases it is desirable to further enhance the efficacy and in vivo tolerability of such agents for an improved treatment, thus inter alia enabling the effective treatment of diseases that have been known to be refractory to the drugs currently known in the art.

Therefore, the technical problem underlying the present invention is to provide more effective and/or more tolerable pharmaceutical compositions that can be used in the treatment of various diseases.

The solution to the above technical problem is achieved by the embodiments characterized in the claims.

In particular, it has been found that combinations of at least two albumin-based drug delivery systems surprisingly produce better therapeutic effects and tolerability in vivo than using combinations of the low-molecular drugs as such.

Therefore, in one aspect the present invention relates to a composition comprising a combination of at least two different albumin-based drug delivery systems, wherein at least one of the two different albumin-based drug delivery systems is selected from albumin-binding prodrugs, albumin drug conjugates, albumin peptide conjugates, albumin fusion proteins, albumin-binding peptide conjugates, albumin drug nanoparticles, and albumin-based antibody constructs.

According to the present invention, the term "composition" is not specifically restricted and in general relates to a combination of at least two components which are present as a mixture or in separate form and which show an additive or synergistic effect when used in a combined manner.

In particular, in the present invention, the term "composition" includes mixtures of the at least two albumin-based drug delivery systems, either in a separable or in a non-separable manner, but also explicitly includes the case where the respective albumin-based drug delivery systems are present as a combination of separate components, e.g. in different containers. For Example, according to the present invention, the composition may be a mixture of at least two different albumin-based drug delivery systems e.g. for simultaneous administration of said systems, or the at least two albumin-based drug delivery systems may be present in separate containers e.g. for sequential administration, wherein the combined use of said systems results in an improved pharmacological effect or improved tolerability, when compared to the separate use of the single drugs.

The same principle applies for compositions comprising more than two components. For example, according to the present invention, a composition comprising three albumin-based drug delivery systems may be present in form of a mixture of these three components, or may be present as a mixture of the first two systems and, in a separate container, of the third system. As an alternative, each of the three albumin-based drug delivery systems may be present in a separate container.

In the present invention, the expression "albumin-based drug delivery system" is not specifically restricted and includes those systems which comprise one or more therapeutically or diagnostically active agents and use albumin, a fragment or a derivative thereof, as a protein carrier to improve the delivery of the drug to the site of action. According to the present invention, said albumin-based drug delivery systems include those cases where a therapeutically or diagnostically active agent is physically and/or chemically bound to albumin, or is capable of binding thereto. The binding of the drug or its derivative may for example take place ex vivo to exogenous albumin, i.e. before administering the albumin-based drug delivery system to the patient, or may take place in vivo, i.e. after the therapeutically or diagnostically active agent has been administered to the patient. Examples of albumin-based drug delivery systems according to the present invention include those e.g. disclosed in B. Elsadek, F. Kratz: "Albumin as a drug carrier—new applications on the horizon", *J. Controlled Release*, 2011, 157, pp. 4 to 28. Specific examples of albumin-based drug delivery systems according to the present invention include Abraxane™, which is an albumin-paclitaxel nanoparticle, and aggregated albumin nano- or microparticles, drug-albumin conjugates as well as albumin-binding antibody constructs such as single chain antibodies with high-affinity albumin-binding peptide domains, camelid anti-HSA trivalent nanobodies, conjugates of proteins with albumin-binding domain antibodies and albumin fusion proteins where the protein is an antibody, an antibody fragment or a cytokine. A further specific example of the albumin-based drug delivery systems of the present invention includes albumin-binding prodrugs.

Herein, the term "different" means that the at least two different albumin-based drug delivery systems comprised in the composition of the present invention are not identical and at least differ in one aspect, such as the molecular structure of at least one of the components, the ratio and amount of the respective components, the drugs included therein, the mode of interaction with the albumin carrier, etc. For example, the composition of the present invention may contain two albumin-based drug delivery systems which are identical except that different drugs are included therein, such as two different cytostatic agents, or a cytostatic agent and an MDR modulator. According to another example, the composition as defined above may comprise a combination of an albumin-binding antibody construct as one albumin-based drug delivery system, and an albumin-binding prodrug, e.g. containing a cytostatic agent, as another albumin-based drug delivery system. According to a further example, the composition as defined above may comprise a combination of an albumin-drug nanoparticle as one albumin-based drug delivery system, and an albumin-binding prodrug, e.g. containing a cytostatic agent, as another albumin-based drug delivery system.

According to the present invention, the source of the albumin present in or used for the albumin-based drug delivery systems can for example be endogenous or exogenous human serum albumin or human recombinant albumin or a fragment of albumin.

One embodiment of the present invention relates to a composition as defined above, wherein at least one of said at least two different albumin-based drug delivery systems is an albumin-binding prodrug comprising an albumin-binding group, a drug, and a linker that can be cleaved hydrolytically, reductively, enzymatically, or in a pH-dependent manner.

Another embodiment of the present invention relates to a composition as defined above, wherein at least two of said at least two different albumin-based drug delivery systems are albumin-binding prodrugs, each comprising an albumin-binding group, a drug, and a linker that can be cleaved hydrolytically, reductively, enzymatically, or in a pH-dependent manner.

According to the present invention, the drug in each of the albumin-based drug delivery systems may be the same or may be different. The same applies to compositions which comprise more than two, i.e. three, four, five or more albumin-based drug delivery systems. In such cases, each of said albumin-based drug delivery systems may contain a different drug or the same drug, or some may contain the same drug while others contain a different drug. In such a way, it is possible to construct a tailormade composition which is individually adjusted to the therapeutic and/or diagnostic needs.

The term "prodrug" as used herein relates to any form of a drug which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part of the prodrug at the site of action by hydrolytic, enzymatic and/or pH-dependent cleavage.

According to the present invention, there is no specific restriction as to how the components of the albumin-binding prodrug of the composition of the present invention, i.e. the albumin-binding group, the drug, and the cleavable linker are connected to each other, as long as the drug is bound to the cleavable linker, either directly or through a spacer group, and the biological function of the albumin-binding group and the drug are not negatively affected by the structural setup. The molecular structure of the albumin-binding prodrug of the composition of the present invention may, for example, have a linear form or a branched form or is present in a circular form.

According to the present invention, there is no specific restriction concerning the structural setup of the albumin-binding prodrug of the composition of the present invention, i.e. the way the constituents of the above-defined prodrug are chemically bonded together. In particular, the albumin-binding prodrug of the composition according to the present invention may contain one or more spacers in any position between the constituents of the above-defined prodrug, i.e. the albumin-binding group may for example be bound to the rest of the prodrug through a spacer or, as another example, the drug may be bound to the cleavable linker through a spacer. Furthermore, the function of e.g. the cleavable linker may be incorporated in such a spacer, i.e. a spacer may be used between the drug and the rest of the albumin-binding prodrug which can also serve as the cleavable linker. It is also possible to bind the drug, the cleavable linker, and/or the albumin-binding group to a central group, which may be linear, branched or cyclic, such as a peptide, a sugar, a heterocyclic group, or any inorganic or organic compound suitable to bind one or more of the constituents of the prodrug. Structural examples of the albumin-binding prodrugs usable in the composition as defined above include linear constructs such as (drug)-(cleavable linker)-(albumin-binding group), (drug)-(spacer)-(cleavable linker)-(albumin-binding group), (drug)-(cleavable linker)-(spacer)-(albumin-binding group), or (drug)-(spacer)-(cleavable linker)-(spacer)-(albumin-binding group).

The term "albumin-binding group" as used herein is not specifically restricted and relates to any functional group which is capable of binding to albumin by any mechanism, such as covalent and non-covalent binding. According to the present invention, the term "albumin-binding group" may include any protein-binding group which is inter alia or exclusively capable of binding to albumin, a fragment or a derivative thereof. For example, the albumin-binding group may be a chemical group capable of binding to an amino, a hydroxy or a thiol group of albumin. Preferred examples of an albumin-binding group according to the present invention are a maleimide group, a halogenacetamide group, a halogenacetate group, a pyridylthio group, a vinylcarbonyl group, an aziridin group, a disulfide group, a substituted or unsubstituted acetylene group, a thiol group, and a hydroxy-succinimide ester group. In a particularly preferred embodiment of the composition of the present invention, the albumin-binding group is a maleimide group. The albumin-binding group may, for example, include functional groups, such as —COOH or —SO$_3$H, that can be activated by standard coupling agents, e.g. dicyclocarbodiimides, acid chlorides, or peptide coupling reagents (e.g., BOP, HATU, PyBOP).

Further examples of said albumin-binding group include compounds or derivatives of phthalocyanines, coumarins, flavonoids, tetracyclines, naphthalenes, aryl- and heteroaryl-carboxylic acids, lipids and fatty acids, for example long-chain fatty acids such as $C_{10}$-$C_{20}$ fatty acids or $C_{10}$-$C_{20}$ alkyl amines, cyclic or linear tetrapyrroles and organometallic compounds thereof, for example porphyrins and protoporphyrins (such as bilirubin, hematin and derivatives thereof), aromatic acid derivatives substituted with 2-5 halogen atoms (e.g. F, Cl, Br or I) such as iophenoxic acid, organic dyes, for example Evans blue and bromcresol dyes such as bromcresol green and bromcresol purple, and the tryptophan and thyroxine analog compounds as well as derivatives of the above-indicated classes of compounds. Furthermore, according to the present invention, said organic dyes and their derivatives used as albumin-binding groups can be chemically modified or derivatized before or after binding to the therapeutically and/or diagnostically active substance or to the spacer molecule, whereby however the binding behavior to albumin is maintained as compared with the unmodified compound. As an example, a dye used as an albumin-binding group, e.g. an azo dye, may be derivatized by the above-indicated chemical modification, for example by reduction of the azo group or by replacement of the azo group by a C—C single bond or a C—C double bond, in such a way that it is no longer colored.

One or several prodrugs can be bound to any suitable albumin-based carrier such as albumin or fragments and derivatives thereof. The albumin-based carrier in general contains suitable functional groups such as hydroxy, amino or thiol groups to bind the albumin-binding prodrug. If necessary, these can be introduced in the carrier molecule by chemical modification through techniques known to those skilled in the art.

In a preferred embodiment, the albumin-binding group of the albumin-binding pro-drugs usable in the composition according to the present invention allows said albumin-binding prodrugs to bind in situ after administration by e.g. injection to serum albumin, to yield macromolecular prodrugs which carry the drug to the target site. In a particularly preferred embodiment of the composition of the present invention, the albumin-binding group of the above-defined prodrug binds in situ to cysteine-34 of albumin. According to the present invention, the term "in situ" includes the binding of the albumin-binding prodrug of the composition according to the present invention to serum albumin inside the organism to which said prodrug has been administered.

The term "cleavable linker" as used herein relates to any linker which can be cleaved physically or chemically. Examples for physical cleavage may be cleavage by light, radioactive emission or heat, while examples for chemical cleavage include cleavage by redox-reactions, hydrolysis, pH-dependent cleavage or cleavage by enzymes. Cleavage of the cleavable linker according to the present invention can be performed in vivo, e.g. in the body of a patient, e.g. a human patient.

According to a preferred embodiment of the composition of the present invention, the cleavable linker comprises one or more hydrolytically cleavable bonds, the hydrolysis of which releases the respective drug. Examples for hydrolytically cleavable bonds are ester bonds or metal-complex bonds, such as are present in platinum-dicarboxylate complexes, where a diaminediaquoplatinum(II) complex is liberated.

In another preferred embodiment of the composition of the present invention, the cleavable linker may be cleavable by an enzyme. For example, the cleavable linker of the composition of the present invention may contain at least one peptide bond which preferably lies within a cleavable peptide sequence of a protease. A peptide bond can therefore be implemented by the insertion of a respective peptide sequence into the cleavable linker. Suitable enzymes are, for example, proteases and peptidases, e.g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of proteases according to the present invention are in particular MMP-2, MMP-3 and MMP-9, cathepsin B, H, L and D, plasmin, urokinase, and prostate-specific antigen (PSA). Preferred peptide sequences that are incorporated in the prodrug are: Arg, Arg-Arg, Phe-Arg, Phe-Cit, Ile-Pro, Lys, Lys-Lys, Arg-Lys, Ala-Leu-Ala-Leu (SEQ ID No: 1), Phe-Lys, Phe-Lys-Ala, Val-Cit, Val-Arg, Ala-Phe-Lys, D-Ala-Phe-Lys, Met, Met-Met, Phe-Met, Tyr-Met, Ala-Met, Ala-Phe-Met, Phe-Ala-Met, Ala-Tyr-Met, Phe-Tyr-Met, Ser-Ser-Tyr-Tyr-Ser-Arg (SEQ ID No: 2), Ser-Ser-Tyr-Tyr-Ser-Leu (SEQ ID No: 3), Arg-Ser-Ser-Tyr-Tyr-Ser-Leu (SEQ ID No: 4), Phe-Pro-Lys-Phe-Phe-Ser-Arg-Gln (SEQ ID No: 5), Lys-Pro-Ile-Glu-Phe-Nph-Arg-Leu (SEQ ID No: 6), Gly-Pro-Leu-Gly-Ile-Ala-Gly-Gln (SEQ ID No: 7), Gly-Pro-Leu-Gly-Ile-Ala-Gly-Gln (SEQ ID No: 8), Gly-Pro-Gln-Gly-Ile-Trp-Gly-Gln (SEQ ID No: 9), Gly-Phe-Leu-Gly (SEQ ID No: 10). In addition, the enzymatically cleavable linker may contain a self-immolative linker such as a self-immolative p-aminobenzyloxycarbonyl (PABC) linker or a N-methyl- or symmetric N,N-dimethylethylene linker.

In another embodiment, the cleavable linker according to the present invention contains at least one reductively cleavable bond. One example of such a reductively cleavable bond is the disulfide bond. According to a specific example, the disulfide bond both serves as the albumin-binding group and the cleavable linker.

In another preferred embodiment of the composition of the present invention, the cleavable linker according to the present invention preferably contains at least one acid-labile bond. Examples of acid-labile bonds are ester, acetal, ketal, imine, aconityl, hydrazone, acyl hydrazone and sulfonylhydrazone bonds and bonds containing a trityl group.

In a further preferred embodiment of the composition of the present invention, the cleavable linker comprises a substituted or unsubstituted, branched-chain or straight-chain aliphatic alkyl group with 1 to 20 carbon atoms, which may comprise one or more oxygen or nitrogen atoms, and/or a substituted or unsubstituted aryl residue.

In a particularly preferred embodiment of the composition of the present invention, the cleavable linker is an acyl hydrazone linker.

The term "drug" as used herein relates to any compound which brings about a pharmacological effect either by itself or after its conversion in the organism in question, and thus also includes the derivatives from these conversions. The pharmacological effect of the drugs of the composition according to the present invention can be a single effect only, e.g. a cytostatic effect, or a broad pharmacological spectrum of actions, such as an immunosuppressive and antiphlogistic effect at the same time.

In a preferred embodiment of the composition of the present invention, the drug contained in each of the albumin-based drug delivery systems is independently selected from the group consisting of a cytostatic agent, a cytokine, an immunosup-pressant, an antirheumatic, an antiphlogistic, an antibiotic, an analgesic, a virostatic, an antimycotic agent, a transcription factor inhibitor, a cell cycle modulator, an MDR modulator, a proteasome or protease inhibitor, an apoptosis modulator, an enzyme inhibitor, an angiogenesis inhibitor, a hormone or hormone derivative, an antibody or a fragment thereof, a therapeutically or diagnostically active peptide, a radioactive substance, a light emitting substance, or a light absorbing substance.

In a preferred embodiment of the composition of the present invention, the drug contained in each of the albumin-based drug delivery systems is a cytostatic agent independently selected from the group consisting of N-nitrosoureas; the anthracyclines doxorubicin, 2-pyrrollinoanthracycline, morpholinoanthracycline, diacetatoxyal-kylanthracycline, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluoridine, cytarabine, cladribine, fludarabine, pentostatine, gemcitabine, and thioguanine, and any derivatives thereof; the folic acid antagonists methotrexate, raltitrexed, pemetrexed, and plevitrexed, and any derivatives thereof; the taxanes paclitaxel and docetaxel, and any derivatives thereof; the camptothecins topotecan, irinotecan, SN-38, 10-hydroxycamptothecin, GG211, lurtotecan, 9-aminocamptothecin and camptothecin, and any derivatives thereof; the Vinca alkaloids vinblastine, vincristine, vindesine, and vinorelbine, and any derivatives thereof; calicheamicins and and derivatives thereof; maytansinoids and any derivatives thereof; auristatins and any derivatives thereof; epothilones and any derivatives thereof; bleomycin, dactinomycin, plicamycin, miromycin C and cis-configured platinum(II) complexes, or any derivatives thereof.

Especially suitable cytokines according to the present invention are, for example, interleukin-2, interferon α-2a, interferon α-2b, interferon β-1a, interferon β-1b, interferon γ-1b, tumor necrosis factor, and any derivatives thereof.

Especially suitable immunosuppressants according to the present invention are, for example, cyclosporin A, tacrolimus, sirolimus, everolimus, mycophenolatmofetil, and any derivatives thereof.

Especially suitable antirheumatics according to the present invention are, for example, methotrexate, leflunomid, sulfasalazine, chloroquine, and any derivatives thereof.

Especially suitable antiphlogistic and/or analgesic agents according to the present invention are, for example, salicylic acid derivatives such as for example acetylsalicylic acid, and any derivatives thereof; drug derivatives having an acetic or propionic acid group such as diclofenac or, respectively, naproxen, and aminophenol derivatives such as for example paracetamol.

Especially preferred antibiotics according to the present invention are, for example, sulfanilamide, sulfacarbamide and sulfamethoxydiazine, and any derivatives thereof; penicillins, for example 6-aminopenicillanic acid, penicillin G as well as penicillin V, and any derivatives thereof; isoxazolylpenicillins such as oxacillin, cloxacillin and clucloxacillin, and any derivatives thereof; α-substituted benzylpenicillins such as ampicillin, carbenicillin, pivampicillin, amoxicillin, and any derivatives thereof; acylaminopenicillins, for example mezlocillin, azlocillin, piperacillin, apalcillin, and any derivatives thereof; amidinopenicillins, for example mecillinam; atypical β-lactams such as imipenam and aztreonam; cephalosporins, for example cephalexin, cefradin, cefaclor, cefadroxil, cefixime, cefpodoxime, cefazolin, cefazedone, cefuroxime, cefamandole, cefotiam, cefoxitin, cefotetan, cefmetazole, latamoxef, cefotaxmine, ceftriaxone, ceftizoxime, cefmonoxime, ceftazidime, cefsulodin and cefoperazone, and any derivatives thereof; tetracyclines such as tetracycline, chlorotetracycline, oxytetracycline, demeclocycline, rolitetracycline, doxycycline, minocycline, and any derivatives thereof; chloramphenicols such as chloramphenicol and thiamphenicol, and any derivatives thereof; gyrase inhibitors, for example nalidixic acid, pipemidic acid, norfloxacin, ofloxacin, ciprofloxacin and enoxacin, and any derivatives thereof; and antituberculotics such as isoniazid, and any derivatives thereof.

Especially preferred virostatic agents according to the present invention are, for example, nucleoside analogs such as acyclovir, ganciclovir, idoxuridine, ribavirin, vidaribine, zidovudine, didanosine and 2',3'-dideoxycytidine (ddC), and any derivatives thereof, as well as amantadine.

Especially suitable antimycotic agents according to the present invention are, for example, amphotericin B, and any derivatives thereof.

Especially preferred MDR modulators according to the present invention are, for example, verapamil, dihydropyridins, cyclosporin A and D, tacrolismus, rapamyin, digoxin, digitoxin, quinidin, lovastatin, atorvastin, analogues of reserpine, trifluoroperazine, pervilleines A-F, valspodar, dexverapamil, biricodar, bepridil, erythromycin, levofloxacin, losartan, morphin, rifampin, phenytoin, colchicin, rhodamin 123, amprenavir, indinavir, nelfinavir, saqunavir, ritonavir, XR9576, LY335979, OC-144093, R101933, GF120918, ONT-093, MS-209, S-9788, reversin 205 and 121, or any related derivative.

Especially preferred transcription factor inhibitors according to the present invention are, for example, compounds that inhibit activation of NF-κB such as alpha-lipoic acid, alpha-tocopherol, anetholdithioithione (ADT), butylated hydroxyanisole (BHA), cepharanthine, caffeic acid phenethyl ester (3,4-dihydroxycinnamic acid, CAPE), catechol derivatives, diethyldithiocarbamate (DDC), diferoxamine, dihydrolipoic acid, disuifram, dimethyldithiocarbamates (DMDTC), curcumin (diferuloylmethane), EPC-K1 (phosphodiester compound of vitamin E and vitamin C), epigallocatechin-3-gallate (EGCG; green tea polyphenols), ethylene glycol tetraacetic acid (EGTA), glutathione, L-cysteine, lacidipine, melatonin, N-acetyl-L-cysteine (NAC), nordihydroguaiaritic acid (NDGA), phenanthrolines, pyrrolinedithiocarbamate (PDTC), quercetin, tepoxaline (5-(4-chlorophenyl)-N-hydroxy-(4-methoxyphenyl)-N-methyl-1H-pyrazole-3-propan-amide), vitamin C, vitamin E derivatives, alpha-torphryl succinate, alpha-torphryl acetate, PMC (2,2,5,7,8-pentamethyl-6-hydroxychromane), benzyiso-cyanate, resveratol, genistein, lupeol, lycopene, panepoxydone, epoxyquinomicin C, dehydroxymethylepoxyquinomicin (DHMEQ), cycloepoxydon, gliotoxin, as well as 1-K B-alpha phosphorylation and/or degradation inhibitors such as PS-1,145, aspirin, salicylic acid, BAY-11-7082 (E3 [(4-methylphenyl)-sulfonyl]-2-propenenitrile), BAY-11-7085 (E3[(4-t-butylphenyl)-sulfonyl]-2-propenenitrile), cycloepoxydon; 1-hydroxy-2-hydroxymethyl-3-pent-1-enylbenzene, ibuprofen, prostaglandin A1, sanguinarine (pseudochelerythrine, 13-methyl[1,3]-benzodioxolo-[5,6-c]-1,3-dioxolo-4,5 phenanthridinium), sulfasalazine, sulindac, capsaicin (8-methyl-N-vanillyl-6-nonenamide), emodin (3-methyl-1,6,8-trihydroxyanthraquinone), erbstatin (tyrosine kinase inhibitor), estrogen (E2), gliotoxin, genistein, resiniferatoxin, and miscellaneous inhibitors of NF-κB such as beta-amyloid protein, glucocorticoids (dexamethasone, prednisone, methylprednisolone), leptomycin B (LMB), o,o'-bismyristoyl thiamine disulfide (BMT), ADP ribosylation inhibitors e.g., nicotinamide, 3-aminobenzamide, bi-, tri, or tetracyclic lactames, 1,8-naphtalimide derivatives, phenanthridin-6-ones, 3,4-dihydro-5-methyl-isoquinolin-1 (2H)-one, benzoxazole-4-carboxamide, 1,6-naphthyridine-5 (6H)-ones, quinazolin[3,4-d]pyrimidin-4(3H)-ones, 1,5-dihydroxyisoquinoline, 2methyl-quinazolin-4[3H]-ones, 1,11b-dihydro-[2H]benzopyrano [4,3,2-de]isoquinolin-3-one, atrial natriuretic peptide (ANP), atrovastatin (HMG- CoA reductase inhibitor), calcitriol (1a,25-dihydroxyvitamine D3), E3330 (quinone derivative), herbimycin A, hypericin, hydroquinone (HQ), KT-90 (morphine synthetic derivatives), mevinolin, 5'-methylthioadenosine (MTA), pentoxifylline (1-(5'-oxohexyl) 3,7-dimethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin,), silymarin, vasoactive intestinal peptide (VIP), D609 (phosphatidylcholine-phospholipase C inhibitor), RO31-8220 (PKC inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N''-4-pyridylguanidine), sesquiterpene lactones such as parthenoilde, helenalin, miller-9E-enolid and budlein A.

Especially preferred proteasome and protease inhibitors according to the present invention are, for example, peptide aldehydes: ALLnL (N-acetyl-leucinyl-leucinylnorleucynal, MG101), LLM (N-acetyl-leucinyl-leucinyll-methional), Z-LLnV (carbobenzoxyl-leucinyl-leucinyl-norvalinal, MG115), Z-LLL (carbobenzoxyl-leucinylleucinyl-leucynal, MG132), Z-LLL-B(OH)$_2$ (MG-262), boronic acid derivatives, e.g. PS-273, PS-293, PS-296, PS-303, PS-305, PS-313, PS-321, PS-325, PS-334, PS-341, PS-364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosine-ethylester), DCIC (3,4-dichloroisocoumarin), DFP (diisopropyl-uorophosphate), TPCK (N-alpha-tosyl-L-phenylalanine chloromethyl ketone), TLCK (N-alpha-tosyl-L-lysine chloromethyl ketone), FK506 (Tacrolimus), Cyclosporin A.

Especially preferred apoptosis modulators according to the present invention are, for example, farnesyl transferase inhibitors, e.g. R115777, SCH66336, BMS214662, Imatinib, 17-AAG, EGFR inhibitors, e.g., ZD1839, MEK inhibitors, e.g., PD 032590, RAF inhibitors e.g., BAY43-9006, erlotinib, PKC inhibitors, e.g. UCN-01, PKC-412, Bryostatin, ISIS-3521, LY333531, safingol, CGP-41251 (midostaurin), HDAC inhibitors, e.g., suberoyl-3-aminopyridineamide hydroxamic acid, lonidamine, apoptin, survivin, rapamycin, CCI-779, RAD001 (everolimus), PXD101, tyrosine kinase inhibitors, e.g. Iressa, OSI-774, STI-571, inhibitors of enzymes in the mitogen-activated protein kinase pathway e.g., PD-098059, U-0126.

Especially preferred cell cycle modulators according to the present invention are, for example, flavopiridol, bryostain-1, roscovitine, BMS-387032, perifosine, or lovastatin.

Especially preferred enzyme inhibitors according to the present invention are, for example, inhibitors of γ-glutamyl cystine synthetase e.g., buthione, sulfoxime.

Especially preferred angiogenesis inhibitors according to the present invention are, for example, thalidomide, endostatin, celecoxib, ABT-510, combretastatin A4, dalteparin, dimethylxanthenone acetic acid, lenalidomide, LY317615 (enzastaurin), PPI-2458, ADH-1 (exherin), AG-013736, AMG-706, AZD2171, Bay 43-9006 (sorafenib), BMS-582664, CHIR-265, GW786034 (pazopanib), PI-88, PTK787/ZK 222584 (vatalanib), RAD001 (everolimus), SU11248 (sunitinib), suramin, XL184, ZD6474, ATN-161, or EMD 121974 (cilenigtide).

Especially preferred hormones or hormone derivatives according to the present invention are, for example, aminogluthemid, buserilin, cyproteronacetate, droloxifen, ethinylestradiol, flutamid, formesta, fosfestrol, gestonoroncaproate, goserilin, leuprolein, lynestrenol, medrogeston, medroxyprogesteronacetate, megestrolactetate, octreotid, tamoxifen, toremifin, triptorelin, anastrazole, exemestane, or letrozone.

According to the present invention, there is no specific limitation regarding the combination of drugs in the composition as defined above. For example, two or more albumin-based drug delivery systems which contain drugs with similar pharmacological action, such as two or more cytostatic agents, two or more antibody (fragments) or two or more MDR modulators may be combined. On the other hand, combinations of different types of drugs may be comprised in the composition as defined above, in case such a combination is suited to improve the therapeutic effect of the overall composition.

In a preferred embodiment of the composition of the present invention, the drug in each of the said albumin-based drug delivery systems may be the same or a different specific cytostatic agent, such as doxorubicin, methotrexate, paclitaxel, docetaxel, or rapamycin.

For preparing the albumin-binding prodrug of the composition of the present invention the drug is bound to a linker through an acid-sensitive and/or hydrolytically and/or reductively and/or enzymatically cleavable bond. This derivatization is carried out with a suitable functional group of the respective drug which is a HO—, H$_2$N—, HOOC—, HO$_3$S—, or carbonyl group. If the drug does not contain a suitable functional group, then it is introduced through chemical modification, i.e. the above-mentioned drugs additionally include all derivatives that possess a HO—, H$_2$N—, HOOC—, HO$_3$S—, and/or carbonyl group.

A further embodiment of the present invention relates to a composition as defined above, wherein at least one of said at least two different albumin-based drug delivery systems is an albumin-binding prodrug comprising an albumin-binding group, a drug, and a linker that can be cleaved hydrolytically, reductively, enzymatically, or in a pH-dependent manner, and wherein at least one of said two different albumin-based drug delivery systems is an albumin-drug nanoparticle.

Specific examples of said albumin-binding nanoparticle include nab-paclitaxel (ABRAXANE® ABI-007, Abraxis BioScience), nab-docetaxel (ABI-008) or nab-rapamycin (ABI-010).

In a further embodiment of the above-defined composition, the at least two different albumin-based drug delivery systems are either present as a mixture, e.g. for simultaneous administration, or are each present in separate containers e.g. for sequential administration.

Herein, the term "simultaneous administration" is not specifically restricted and means that the individual albumin-based drug delivery systems are substantially administered at the same time, e.g. as a mixture or in immediate subsequent sequence.

Moreover, the term "sequential administration" used herein is not specifically restricted and means that the individual albumin-based drug delivery systems are not administered at the same time but one after the other, or in groups, with a specific time interval between administrations.

In a further embodiment, the present invention relates to the above-defined composition, wherein in the sequential administration each of the albumin-based drug delivery systems is administered in specific time interval after the preceding administration. According to the present invention, said time interval may be the same or different between the respective administrations of each of the albumin-based drug delivery systems and may be selected, for example, from the range of 2 minutes to 96 hours, 1 to 7 days or one, two or three weeks. Generally, according to the present invention, the time interval between the administration of the individual albumin-based drug delivery systems may be in the range of a few minutes to hours, such as in the range of 2 minutes to 72 hours, 30 minutes to 24 hours, or 1 to 12 hours. Further examples include time intervals in the range of 24 to 96 hours, 12 to 36 hours, 8 to 24 hours, and 6 to 12 hours.

A specific embodiment of the present invention relates to the above-defined composition, wherein one of said at least two different albumin-based drug delivery systems is the 6-maleimidocaproyl(hydrazone) derivative of doxorubicin (DOXO-EMCH), and wherein one of the at least two different albumin-based drug delivery systems is selected from (i) an albumin-binding prodrug, selected from the methotrexate derivative EMC-D-Ala-Phe-Lys-Lys (.gamma.-MTX)-OH, wherein EMC=6-maleimidocaproic acid, (AW054), (ii) an albumin-drug nanoparticle, selected from nab-paclitaxel (ABRAXANE® ABI-007, Abraxis Bio-Science), nab-docetaxel (ABI-008) or nab-rapamycin (ABI-010), (iii) an albumin-binding antibody construct selected from camelid anti-HSA trivalent nanobodies, and (iv) an albumin fusion protein with interferons or interleukins selected from albinterferon alfa-2b or albuleukin.

The molar ratio of the albumin-based drug delivery systems of the composition of the present invention is not particularly restricted. For example, in case two albumin-based drug delivery systems are combined in the composition as defined above, the molar ratio of said systems may be in the range of 1:500 to 500:1, or of 1:100 to 100:1. According to a further example, the molar ratio is in a range of 1:50 to 50:1, or of 1:20 to 20:1. However, the molar ratio may also be in the range of 1:5 to 5:1, or 1:1. Similar molar ratios apply when using three or more albumin-based drug delivery systems in the composition of the present invention.

Preferably, the composition of the present invention does not contain any additional drug, except for the drugs comprised in each of the at least two different albumin-based drug delivery systems. That is, according to the present invention, it is preferred that the above-defined composition comprises the at least two different albumin-based drug delivery systems, and optionally one or more adjuvants, such as solvents, diluents, etc., but does not contain a drug as such which is not part of said albumin-based drug delivery system.

The present invention further relates to a kit, comprising the composition as defined above, and optionally a pharmaceutically acceptable carrier and/or a pharmaceutically acceptable adjuvant and/or diluent. In the kit of the present invention, the albumin-based drug delivery systems may be present as a mixture e.g. for simultaneous administration, or may be present in separate containers, e.g. for subsequent administration.

In another aspect, the present invention relates to a pharmaceutical composition comprising the composition of the present invention, and optionally a pharmaceutically acceptable carrier and/or a pharmaceutically acceptable adjuvant and/or diluent.

The kit or the pharmaceutical composition of the present invention may for example contain solvents and diluents such as a sodium chloride solution or a solution containing any pharmaceutically acceptable buffers. Moreover, the pharmaceutical composition of the present invention may be in any form suitable for administration to a patient, for example in an injectable form, as a tablet or a capsule, or as a composition for inhalation.

According to a further embodiment of the present invention, the kit or the pharmaceutical composition as defined above are for use in the treatment of a disease selected from the group consisting of cancer, autoimmune diseases, acute or chronic inflammatory diseases, or diseases caused by viruses and/or microorganisms.

In a further aspect, the present invention relates to the use of the composition of the present invention in the manufacture of a medicament for treating a patient suffering from a disease selected from the group consisting of cancer, autoimmune diseases, acute or chronic inflammatory diseases, or diseases caused by viruses and/or microorganisms.

A further aspect of the present invention relates to the composition, the kit, or the pharmaceutical composition as defined above for use in the treatment of a disease selected from the group consisting of cancer, autoimmune diseases, acute or chronic inflammatory diseases, or diseases caused by viruses and/or microorganisms.

In a further aspect, the present invention relates to a method for treating a patient suffering from a disorder or a disease such as cancer, autoimmune diseases, acute or chronic inflammatory diseases, or diseases caused by viruses and/or microorganisms, comprising the step of administering the composition or the pharmaceutical composition as defined above.

Figure 1B:
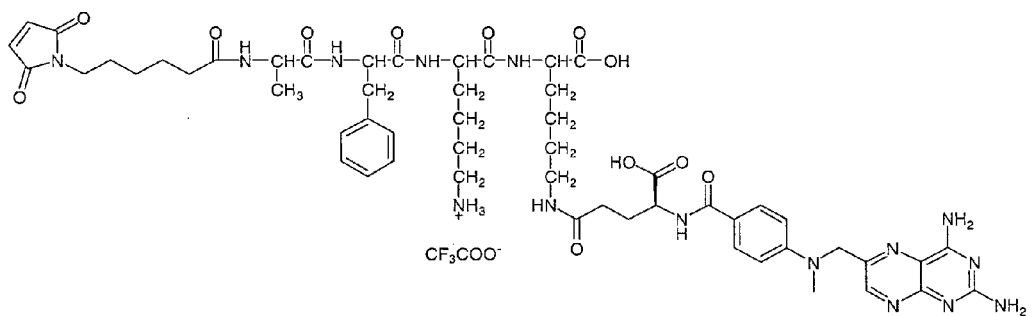

The Figures show:

FIGS. 1A AND 1B: Chemical structure of the albumin-binding prodrug DOXO-EMCH (FIG. 1A) which is the 6-maleimidocaproyl(hydrazone) derivative of doxorubicin, and of the albumin-binding prodrug AW054 (FIG. 1B) which is a methotrexate derivative.

Figure 2:
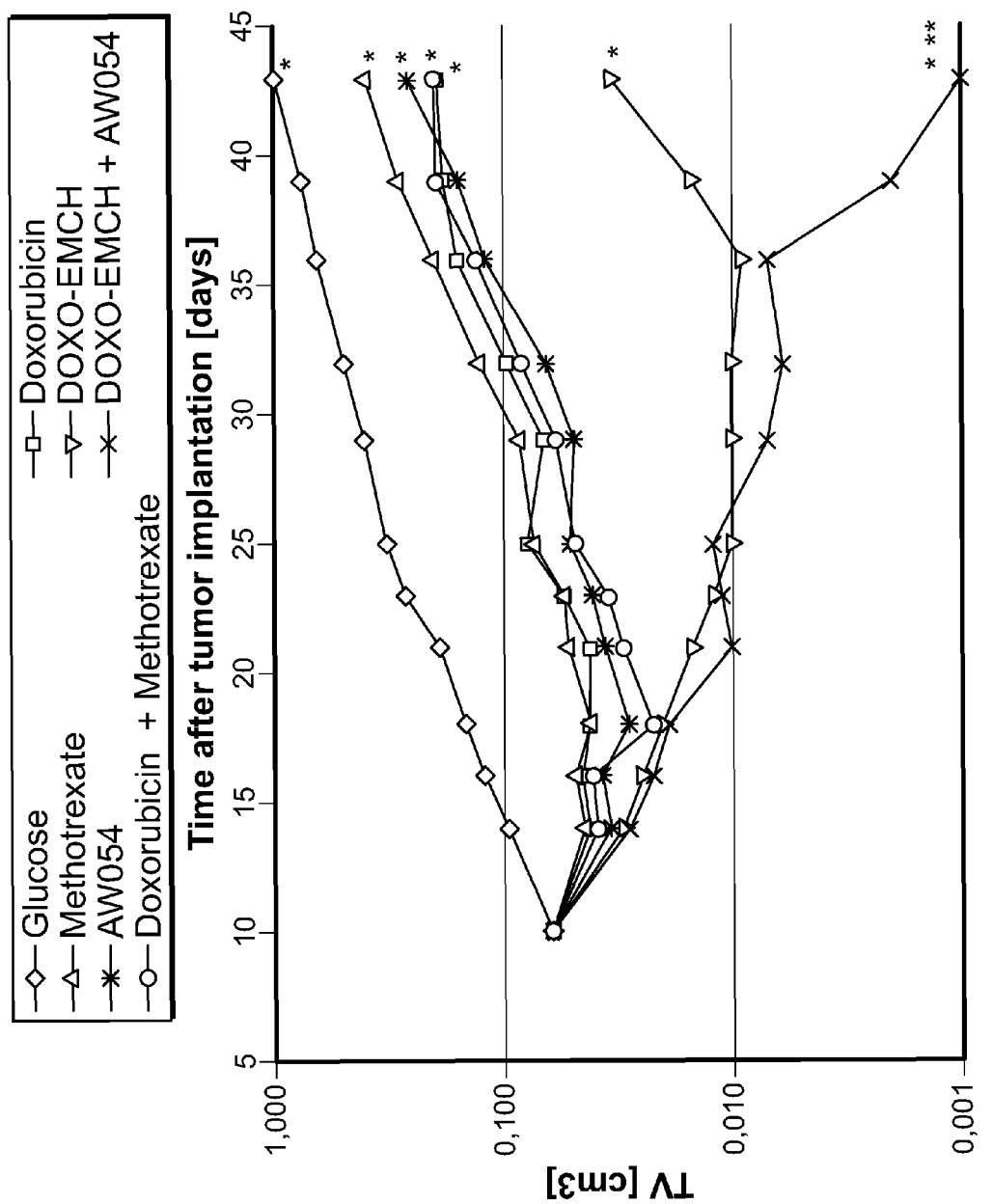

FIG. 2: Therapeutic efficacy of DOXO-EMCH (3×24 mg/kg), AW054 (3×20 mg/kg), and a combination of DOXO-EMCH (3×12 mg/kg) and AW054 (3×10 mg/kg) or of doxorubicin (3×6 mg/kg), of methotrexate (3×125 mg/kg) or a combination of doxorubicin (3×3 mg/kg doxorubicin) and methotrexate (3×62.5 mg/kg) against the MiaPaCa-2 pancreatic carcinoma xenograft model (7 animals per group); tumor volumes are depicted on a logarithmic scale.

Figure 3:
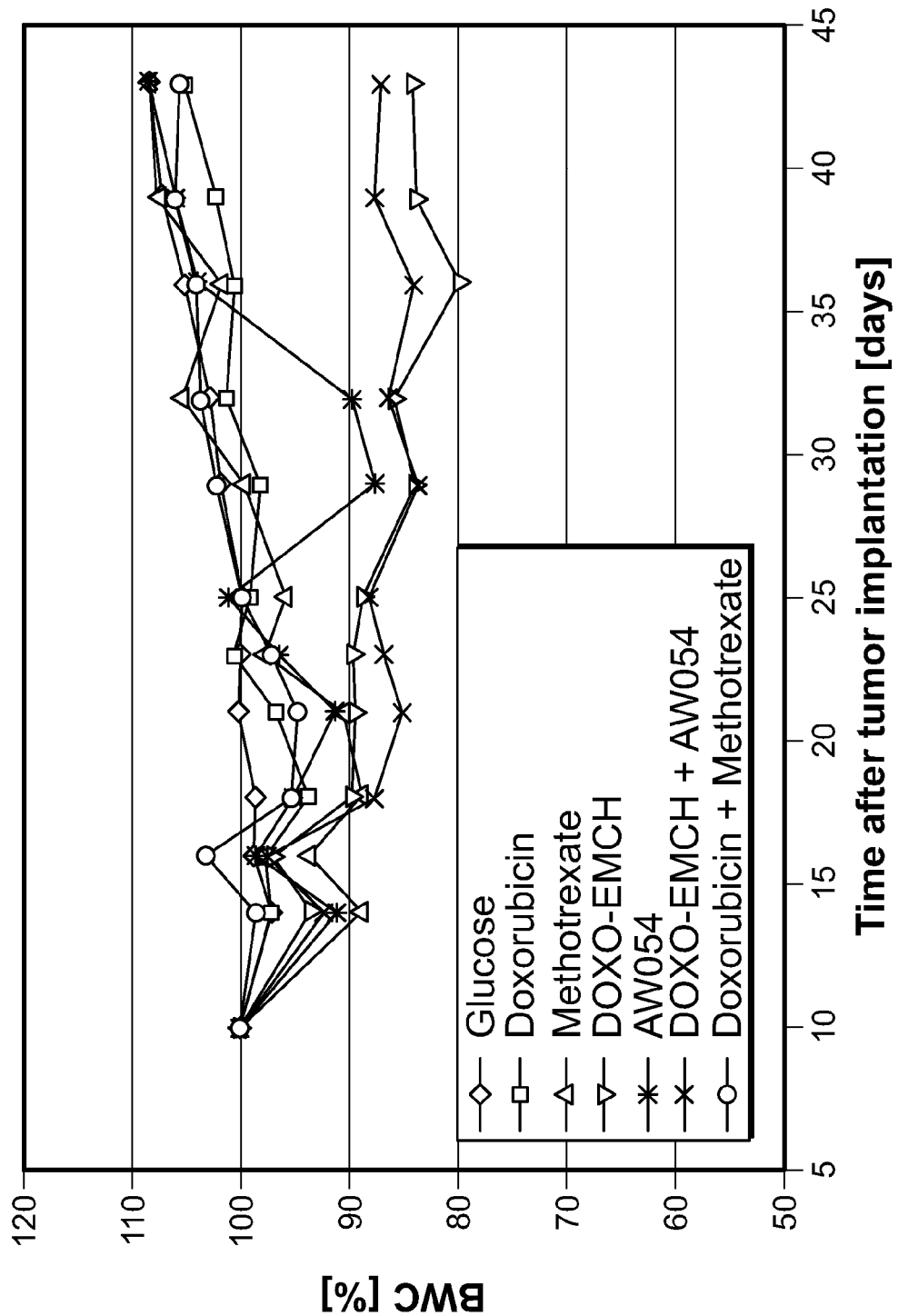

FIG. 3: Body weight curves under therapy with DOXO-EMCH (3×24 mg/kg), AW054 (3×20 mg/kg), and a combination of DOXO-EMCH (3×12 mg/kg) and AW054 (3×10 mg/kg) or of doxorubicin (3×6 mg/kg), of methotrexate (3×125 mg/kg) or a combination of doxorubicin (3×3 mg/kg doxorubicin) and methotrexate (3×62.5 mg/kg) in the MiaPaCa-2 pancreatic carcinoma xenograft model (7 animals per group) are depicted.

The compositions of the present invention surprisingly and advantageously produce an improved efficacy and in vivo tolerability over the use of the drugs as such, and further provide an effective treatment of diseases which have previously been refractory to the therapeutics available in the prior art. Accordingly, it is advantageously possible to efficiently treat a great variety of diseases by combining at least two albumin-based drug delivery systems, such as albumin-binding prodrugs, whereby the advantageous properties of said drugs can be improved beyond the properties of the individual drugs alone.

The present invention will now be further illustrated in the following example without being limited thereto. Many further combinations according to the present invention can be realized as outlined above.

EXAMPLE

Example: Evaluation of the Antitumor-Efficacy of a Combination of Two Albumin-Binding Prodrugs The antitumor efficacy of a combination of the 6-maleimidocaproyl(hydrazone) derivative of doxorubicin (DOXO- EMCH) and an albumin-binding prodrug of methotrexate, AW054 (see FIGS. 1A and B), that is cleaved by two proteases that are over-expressed in solid tumors, cathepsin B and plasmin was evaluated in the MiaPaCa-2 pancreatic carcinoma xenograft model.

The 6-maleimidocaproyl(hydrazone) derivative of doxorubicin (DOXO-EMCH) (FIG. 1A) is an albumin-binding prodrug of doxorubicin that binds rapidly to the cysteine-34 position of circulating albumin after administration and is taken up by solid tumors. Following tumor uptake, doxorubicin is cleaved in the acidic environment of tumor tissue, either extra- or intracellularly. DOXO-EMCH has an maximum tolerated dose (MTD) of 3×24 mg/kg doxorubicin equivalents in nude mice and has shown superior efficacy over free doxorubicin in several xenograft and orthotopic tumor models (F. Kratz et al. (2002): Probing the Cysteine-34 Position of Endogenous Serum Albumin with Thiolbinding Doxorubicin Derivatives: Improved Efficacy of an Acid-sensitive Doxorubicin Derivative with Specific Albumin-binding Properties Compared to the Parent Compound, *J. Med. Chem.* 45, 5523-5533; R. Graeser et al. (2009): INNO-206, the (6-maleimidocaproyl hydrazone derivative of doxorubicin); and R. Graeser, N. Esser, H. Unger, I. Fichtner, A. Zhu, C. Unger, F. Kratz (2010): INNO-206, the (6-maleimidocaproyl hydrazone derivative of doxorubicin), shows superior antitumor efficacy compared to doxorubicin in different tumor xenograft models and in an orthotopic pancreas carcinoma model, *Investigational New Drugs* 28, 14-19).

AW054, i.e. EMC-D-Ala-Phe-Lys-Lys(γ-MTX)-OH (EMC=6-maleimidocaproic acid), rapidly binds to the cysteine-34 position of circulating albumin after administration to form a conjugate which is stable in human plasma. Due to two lysine residues it can be cleaved by cathepsin B and plasmin, two enzymes which are found in high levels in solid tumors. After binding to endogenous albumin, AW054 accumulates in tumor tissue and tumor cells where a methotrexate-lysine derivative is released either extra- or intracellularly by plasmin and cathepsin B, respectively (A. Warnecke, I. Fichtner, G. Sass, F. Kratz (2007): Synthesis, cleavage profile, and antitumor efficacy of an albumin-binding prodrug of methotrexate that is cleaved by plasmin and cathepsin B., *Arch. Pharm., Pharm. Med. Chem.* 340, 389-395). AW054 has a MTD of 3×20 mg/kg (methotrexate equivalents) and is superior compared to methotrexate (MTD 3×125 mg/kg) in an ovarian carcinoma xenograft model (OVCAR3) (A. Warnecke, I. Fichtner, G. Sass, F. Kratz (2007): Synthesis, cleavage profile, and antitumor efficacy of an albumin-binding prodrug of methotrexate that is cleaved by plasmin and cathepsin B., *Arch. Pharm., Pharm. Med. Chem.* 340, 389-395).

The combination of DOXO-EMCH with AW054 was evaluated in comparison to the respective albumin-binding prodrugs alone as well as to the conventional drugs doxorubicin and methotrexate and to a combination of doxorubicin and methotrexate in the MiaPaCa-2 pancreatic carcinoma xenograft model.

The experiment in the ovarian carcinoma MiaPaCa-2 xenograft model was carried out as follows:

In vivo efficacy studies in the MiaPaCa-2 xenograft model were carried out with doxorubicin, the 6-maleimidocaproyl (hydrazone) derivative of doxorubicin (DOXO-EMCH), the albumin-binding prodrug of methotrexate AW054, a combination of the 6-maleimidocaproyl(hydrazone) derivative of doxorubicin (DOXO-EMCH) and the albumin-binding prodrug of methotrexate AW054, doxorubicin, methotrexate and a combination of doxorubicin and methotrexate.

DOXO-EMCH was dissolved in sterile 10 mM sodium phosphate, 5% D-(+)-glucose (pH 5.8) and the respective dose administered intravenously within 30 minutes after dissolution. All doses of DOXO-EMCH and AW054 administered in the studies are stated in doxorubicin and methotrexate equivalents, respectively. Adrimedac® from medac, Germany, was used as the doxorubicin reference (c=2 mg/mL). Methotrexate (Sodium salt from medac) was used as a stock solution (12.5 mg methotrexate/mL in 5% D-Glucose from Braun, sterile). The stock solution AW054 for intravenous administration was 2.0 mg AW054/mL in 5% D-Glucose from Braun, sterile.

For in vivo testing in the MiaPaCa-2 xenograft model, female NMRI: nu/nu mice (Taconic, Denmark) were used. The mice were held in individually ventilaged cages (IVC) under sterile and standardized environmental conditions (25±2° C. room temperature, 50±10% relative humidity, 12 hour light-dark-rhythm). They received autoclaved food and bedding (ssniff, Soest, Germany) and acidified (pH 4.0) drinking water ad libitum. All animal experiments were performed under the auspices of the German Animal Protection Law.

MiaPaCa-2 cells ($5×10^6$ cells/mouse) were transplanted subcutaneously (s.c.) into the left flank region of each mouse on day zero. Mice were randomly distributed to the experimental groups (7 mice per group). Treatment was initiated at day 10 when the tumors were grown to a size of ~60 mm³. Mice were treated on a weekly schedule with 3×6 mg/kg doxorubicin (MTD), 2×125 mg/kg methotrexate (MTD), 3×24 mg/kg DOXO-EMCH (doxorubicin equivalents) (MTD), 3×20 mg/kg AW054 (methotrexate equivalents) (MTD), and a combination of 3×12 mg/kg DOXO-EMCH and 3×10 mg/kg AW054 or a combination of 3×3 mg/kg doxorubicin and 3×62.5 mg/kg methotrexate. All compounds were injected once a week for three weeks (days 10, 17, 24). The injection volume was 0.2 mU20 g body weight. Tumor size was measured twice weekly with a caliper-like instrument in two dimensions. Individual tumor volumes (V) were calculated by the formula $V=(length×[width]^2)/2$ and related to the values on the first day of treatment (relative tumor volume, RTV). The experiment was ended on day 43. Statistical analysis was performed with the U-test (Mann and Whitney) with $p<0.05$. The body weight of mice was determined every 3 to 4 days.

Pancreatic cancer has a poor prognosis: For locally advanced and for metastatic disease, which collectively represent over 80% of individuals, median survival is approximately 10 and 6 months, respectively, when treated with either 5-fluorouracil or gemcitabine.

3×6 mg/kg doxorubicin is the maximum tolerated dose (MTD) in nude mice models. The MTD of methotrexate in nude mice models is 3×125 mg/kg (i.v.). Combination therapy with doxorubicin and methotrexate was carried out at in a three weekly schedule (i.v.) at half of their maximum tolerated dose (MTD), i.e. 3×3 mg/kg for doxorubicin and 3×62.5 mg/kg methotrexate. Both DOXO-EMCH and AW054 were administered simultaneously (i.v.) in a three weekly schedule at half of their maximum tolerated dose (MTD), i.e. 3×12 mg/kg for DOXO-EMCH (doxorubicin equivalents) and 3×10 mg/kg (methotrexate equivalents) and at their respective MTDs, i.e. 3×24 mg/kg for DOXO-EMCH (doxorubicin equivalents) and 3×20 mg/kg for AW054 (methotrexate equivalents) (see the following Table 1).

TABLE 1

Comparison of doses, mortality, and final tumor volume of doxorubicin, DOXO-EMCH, and the combination of DOXO-EMCH and doxorubicin against human Mia-Paca-2 cancer xenografts (median initial tumor volume on day 1 was 0.062 cm$^3$)

| Mice | Compounds | Schedule [days] | Dose (i.v.) [mg/kg/inject.] | toxic death | Tumor volume (day 43) cm$^3$/d 43 |
|---|---|---|---|---|---|
| 7 | Glucose-Phosphate Puffer | 10, 17, 24 | | 0 | 0.992 ± 0.362 - |
| 7 | Doxorubicin | 10, 17, 24 | 6 | 0 | 0.190 ± 0.125* |
| 7 | Methotrexate | 10, 17, 24 | 125 | 0 | 0.396 ± 0.307* |
| 7 | Doxorubicin + Methotrexate | 10, 17, 24 | 3 + 62.5 | 0 | 0.199 ± 0.071* |
| 7 | DOXO-EMCH | 10, 17, 24 | 24 | 1 (d 39) | 0.034 ± 0.064* |
| 7 | AW054 | 10, 17, 24 | 20 | 0 | 0.264 ± 0.226* |
| 7 | DOXO-EMCH + AW054 | 10, 17, 24 | 12 + 10 | 0 | 0.001 ± 0.001* ** |

5 × 10$^6$ MiaPaca-2 cells/mouse, s.c. day 0
*Statistically significant to control (Glucose phosphate buffer treated group)
** Statistically significant to all groups Mann-Whitney test, p < 0.05
NMRI: nu/nu mice, female The efficacy results of the drugs alone and their combination are shown in FIG. 2

Compared to the combination of DOXO-EMCH or AW054 alone, where DOXO-EMCH showed a partial remission (one of the seven mice died on day 39) and AW054 only showed moderate antitumor effects over control animals treated with 5% glucose phosphate buffer (see FIG. 2), the combination of the two albumin-binding prodrugs produced complete remissions and an acceptable body weight loss of −13% at the end of the experiment compared to the starting tumor volume (see FIG. 3).

With respect to antitumor efficacy, the free drugs doxorubicin and methotrexate at their optimal and maximum tolerated doses or as combination of the two drugs only showed moderate antitumor efficacy up to the end of the experiment (day 43) (see FIG. 2).

In summary, treatment with a combination of the two albumin-binding prodrugs DOXO-EMCH at 3×12 mg/kg and AW054 at 3×10 mg/kg was the only therapy schedule which produced complete remissions against subcutaneously growing MiaPaCa-2 pancreatic carcinoma xenografts, this effect being statistically significant (p<0.05, Mann-Whitney test) compared to all other groups. Thus, the treatment combining DOXO-EMCH with AW054 has a distinct advantage over treatment with either DOXO-EMCH or AW054 alone or doxorubicin, methotrexate or a combination thereof with respect to antitumor efficacy.

The invention claimed is:

1. A composition comprising a combination of at least two different albumin-binding prodrugs, wherein one of said at least two different albumin-binding prodrugs is the 6-maleimidocaproyl(hydrazone) derivative of doxorubicin (DOXO-EMCH), and wherein one of the at least two different albumin-binding prodrugs is the methotrexate derivative EMC-D-Ala-Phe-Lys-Lys(γ-MTX)-OH, wherein EMC=6-maleimidocaproic acid, (AW054).

2. The composition according to claim 1, wherein the at least two different albumin-based prodrugs are each present in separate containers to be sequentially administered.

3. A pharmaceutical composition comprising the composition of claim 1 and a pharmaceutically acceptable carrier and/or a pharmaceutically acceptable adjuvant and/or diluent.

* * * * *

```
                        SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Preferred peptide equence incorporated in the
      prodrug

<400> SEQUENCE: 1

Ala Leu Ala Leu
1

<210> SEQ ID NO 2
<211> LENGTH: 6
<212> TYPE: PRT
<213> ORGANISM: Artificial Sequence
<220> FEATURE:
<223> OTHER INFORMATION: Preferred peptide equence incorporated in the
      prodrug

<400> SEQUENCE: 2

Ser Ser Tyr Tyr Ser Arg
1               5

<210> SEQ ID NO 3
<211> LENGTH: 6
```

```
<212> TYPE: PRT
<213> ORGANISM: Artificial Sequence
<220> FEATURE:
<223> OTHER INFORMATION: cleavable linker

<400> SEQUENCE: 3

Ser Ser Tyr Tyr Ser Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 4

Arg Ser Ser Tyr Tyr Ser Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 5

Phe Pro Lys Phe Phe Ser Arg Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug
<220> FEATURE:
<221> NAME/KEY: nph
<222> LOCATION: (6)..(6)
<223> OTHER INFORMATION: x = nitrophenylalanine

<400> SEQUENCE: 6

Lys Pro Ile Glu Phe Xaa Arg Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 7

Gly Pro Leu Gly Ile Ala Gly Gln
1               5

<210> SEQ ID NO 8
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug
```

```
<400> SEQUENCE: 8

Gly Pro Leu Gly Ile Ala Gly Gln
1               5

<210> SEQ ID NO 9
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 9

Gly Pro Gln Gly Ile Trp Gly Gln
1               5

<210> SEQ ID NO 10
<211> LENGTH: 4
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 10

Gly Phe Leu Gly
1
```